United States Patent [19]
Hanson

[11] Patent Number: 5,685,711
[45] Date of Patent: Nov. 11, 1997

[54] SELF-LIGATING ORTHODONTIC BRACKETS

[76] Inventor: G. Herbert Hanson, 57 Augusta Street, Hamilton, Ontario, Canada, L8N 1P8

[21] Appl. No.: 568,219

[22] Filed: Dec. 6, 1995

[51] Int. Cl.⁶ ..................................... A61C 7/00
[52] U.S. Cl. .............................................. 433/11
[58] Field of Search ........................ 433/10, 11, 13, 433/14, 17

[56] References Cited

U.S. PATENT DOCUMENTS

| | | | |
|---|---|---|---|
| 3,871,096 | 3/1975 | Walshein | 433/11 |
| 4,144,642 | 3/1979 | Wallshein | 433/11 |
| 4,725,229 | 2/1988 | Miller | 433/11 |
| 5,059,119 | 10/1991 | Snead | 433/8 |
| 5,094,614 | 3/1992 | Wildman | 433/10 |
| 5,516,284 | 5/1996 | Wildman | 433/10 |

FOREIGN PATENT DOCUMENTS

| | | | |
|---|---|---|---|
| 2357573 | 5/1975 | Germany | 433/11 |

*Primary Examiner*—Cary E. O'Connor
*Attorney, Agent, or Firm*—Rogers & Scott

[57] ABSTRACT

An orthodontic bracket comprises a bracket body with a mesial distal extending arch wire slot and a two-armed ligating latch spring member mounted thereon. The two arms comprise a ligating inner portion and a latching outer portion joined by a connecting portion and the spring member is movable between an unlatched slot open position and a latched slot closed position in which the slot is closed by the ligating portion and the spring member is latched to the bracket body by the latching portion. The bracket body may be made as two mirror image parts between which the spring member is mounted, the two body parts thereafter being fastened together. Each body part may carry a cylindrical mesial distal extending pivot post, the spring member being mounted on the posts for pivoting movement relative to the bracket body, the posts and spring member being frictionally engaged as it moves between slot open and closed positions for frictional damping of the pivoting movement. The latches between the spring member and the bracket body may comprise notches in the spring edges that are engaged by latch sears on the body, and preferably the latch sears have cam acting labial faces producing gingival movement until the latches are engaged. Preferably the spring member is made of a nickel titanium shape memory alloy. The bracket body may have one or two hook members for attachment of a traction spring member. It may instead have two pairs of tie wings for reception of an external ligature between which the spring member is disposed.

20 Claims, 5 Drawing Sheets

SELF-LIGATING ORTHODONTIC BRACKETS

FIELD OF THE INVENTION

This invention is concerned with improvements in or relating to self-ligating orthodontic brackets, namely orthodontic brackets which comprise ligating spring means as a permanent part thereof. It is concerned particularly with such brackets of small size and of smooth exterior contour, so as to be specially suitable for use in orthodontic procedures in which they are mounted on the lingual surfaces of the teeth.

REVIEW OF PRIOR ART

The majority of orthodontic procedures employ a plurality of brackets that are attached to respective teeth, increasingly by cementing them to the teeth. Each bracket has a mesial distal extending slot therein, usually of rectangular transverse cross section, and the brackets are connected together using an arch wire, so called because it is preformed to an optimum arch shape corresponding to the desired conformation of the teeth at the conclusion of the procedure. Arch wires of progressively increasing stiffness and, depending on the type of tooth movement to be achieved, frequently also of different cross section, are used one at a time, the wire being retained in the slots by ligating means of some kind. Initially the ligating means usually was a metal wire that was twisted about the bracket and the arch wire; subsequently as elastomeric materials were developed that could withstand the hostile environment of the human mouth, elastomeric hoops or loops have become increasingly commonly used. In another line of development each bracket comprises a permanently mounted self-ligating spring member; specific examples of such brackets are those disclosed and claimed in my U.S. Pat. Nos. 3,772,787; 4,248,588 and 4,492,573, and in my application Ser. No. 08/274,077, filed 12 Jul. 1994, now U.S. Pat. No. 5,586,882 the disclosures of which are incorporated herein by this reference. These brackets are currently in use in the Hanson SPEED System (Trade Mark) and have proven to be very successful.

There is a constant endeavour in orthodontics to provide brackets that are as small and as smooth exteriorly as possible, for cosmetic reasons, and also to reduce as much as possible the likelihood of rough contact between the brackets and the tongue and adjacent tissue of the mouth, with consequent discomfort to the patient. There is also increasing interest in the so-called lingual technique, in which the brackets are mounted on the lingual tooth surfaces, so that they and the wire are concealed from frontal view. This is of special interest to adult patients who are more concerned than children with appearance during the two-three year period required for a typical procedure. Small smooth brackets are particularly needed for this location because of ready access by the tongue, and the natural tendency of the tongue to explore any foreign object in the mouth. Attempts simply to reduce the size of existing brackets are not generally successful, at least partly because changes in scale affects size parameters in different ratios, e.g. areas decrease in square ratio while volumes decrease in cube ratio, with the result that it becomes increasingly difficult, especially with the tiny spring members required in self-ligating brackets, to find materials of the necessary properties.

One example of such a small smooth exterior bracket intended particularly for lingual procedures is that described and claimed in my U.S. Pat. No. 4,698,017, issued 06 Oct. 1987, the disclosure of which is incorporated herein by this reference. These brackets comprise a smoothly contoured body with a mesial distal extending arch wire slot. A latch member of "comma" cross section is accommodated in a recess in the body, and pivots about a mesial distal extending axis between a slot open position and a slot closed position in which the tail of the comma closes the slot mouth with its smoothly curved outer surface facing lingually. A first load spring for applying corrective forces to the arch wire and a second latch spring for the latching operation of the latch member are accommodated totally within the body.

Orthodontics is now a mature profession, and the manufacture of orthodontic equipment is a mature industry, and the ongoing requirement to provide equipment that is efficient, economical and easy to use increasingly has the added requirement to be as inexpensive as possible, especially if orthodontists are to be persuaded to make the changes in their procedures that the adoption of new brackets might entail.

SUMMARY OF THE INVENTION

It is a principal object of the invention therefore to provide new self-ligating brackets.

It is another principal object to provide new self-ligating brackets of small size and of smooth exterior contour, so as to make them specially suitable for use in lingual techniques.

It is a further object to provide such new self-ligating brackets requiring a minimum number of parts and in which the cost of their fabrication is minimized.

In accordance with the invention there is provided an orthodontic bracket intended specially for lingual techniques, the bracket comprising:

- a bracket body having labial, lingual, gingival, occlusal, mesial and distal surface portions, the body having a mesial distal extending arch wire slot opening to the lingual surface portion; and

- a ligating latch spring member comprising a ligating portion and a latching portion joined at adjacent ends by a connecting portion;

- the spring member being mounted on the body for movement between an unlatched slot open position in which the slot opening is open for insertion of an arch wire into the slot, and a latched slot closed position in which the slot opening is closed for retention of an arch wire in the slot by the ligating portion and the spring member is latched in the slot closed position by latching engagement between the latching portion and the bracket body.

Preferably the ligating latch spring member is mounted on the body for pivoting movement thereon on at least one mesial distal extending pivot post about which the spring member connecting portion is wrapped. Preferably also the bracket body has a part cylindrical recess therein;

- the pivot post is cylindrical and is coaxial with the part cylindrical recess to form a chamber of annular transverse cross section between them;

- the spring member connecting portion is part circular in transverse cross section and is movable within the part cylindrical recess;

- and the external radius of the part circular spring member connecting portion is larger than the internal radius of the part cylindrical recess, so that when mounted the connecting portion is strained radially by its resilience to frictionally engage with the inner wall of the part cylindrical recess and with the pivot post for frictional damping of the pivoting movement of the spring member on the pivot post.

The bracket body may be made as two mirror image parts which butt one another at a junction, and between which the ligating latch spring member is mounted, the two body parts being fastened together at their junction to retain the member thereon.

Preferably means for effecting latching engagement between the spring member latching portion and the bracket body comprise notches in the mesial and distal edges of the latching portion adjacent to its free end, and cooperating occlusally extending latch sears on the bracket body which engage in the respective notch to effect the latching, the spring member latching portion free end moving in gingival occlusal direction to engage and disengage the latches.

The ligating latch spring member may be made of a shape memory metal, and preferably is made of a nickel titanium shape memory alloy.

The bracket body may have protruding therefrom a hook member, and preferably two such members, that extends gingivally and either mesially or distally for attachment of a traction spring member and the like to the bracket body.

One form of the bracket may have two pairs of tie wings for the reception and retention of an external ligature;

wherein the pairs of tie wings are spaced mesially distally from one another, and the two wings of each pair extend gingivally and occlusally away from one another; and wherein the ligating latch spring member is disposed on the body between the two pairs of tie wings.

DESCRIPTION OF THE DRAWINGS

Particular preferred embodiments of the invention will now be described, by way of example, with reference to the accompanying diagrammatic drawings, wherein:

FIGS. 11 and 12 are respectively views from the lingual and the mesial of a bracket, showing one way in which brackets of the invention can be provided with hooks for engagement with traction springs and the like;

DESCRIPTION OF THE PREFERRED EMBODIMENTS

In this specification and the appended claims, for convenience in language the brackets and parts thereof are referred to, unless otherwise specified, as they would be used mounted in the upper arch region of a patient's mouth and employed in a technique in which they are attached to the lingual surfaces of the teeth, even though in the majority of the procedures that are employed at this time the brackets are attached to the labial teeth surfaces. The brackets of the invention are of course equally usable in both the lingual and labial techniques, while being particularly intended and suitable for the lingual technique owing to their small size and smooth external contour. As applied to the bracket structure the labial and lingual direction designations are reversed between the two procedures, e.g. the bracket surface referred to as the labial surface in the labial procedure becomes the lingual surface in the lingual procedure, and vice versa, and the arch wire slot opens to the lingual and not the labial.

Similar parts are given the same reference number in all the Figures of the drawings wherever this is appropriate.

Figure 1:
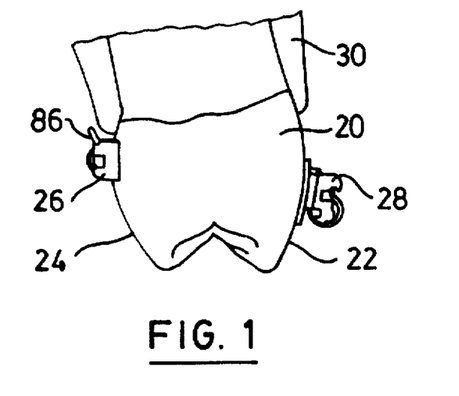
FIGS. 1 through 3 are views from the mesial of different teeth with brackets of the invention cemented to the respective lingual surfaces thereof, showing the different manner in which the bases of the brackets are shaped for their use with the respective tooth, each Figure also showing a bracket of the Hanson SPEED System referred to above cemented to the labial surface of the respective tooth.
Figure 2:
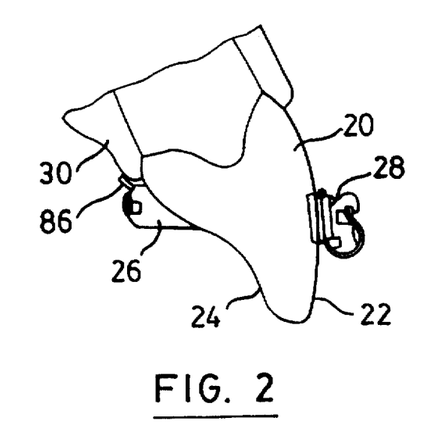
Figure 3:
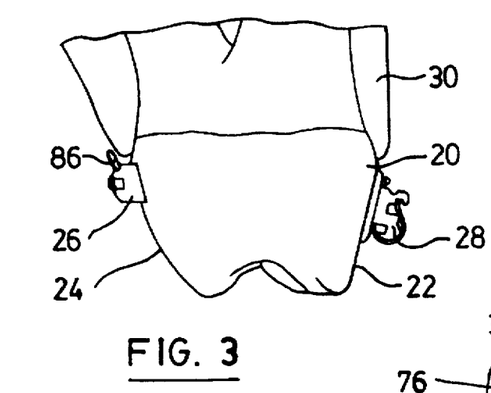
Figure 4:
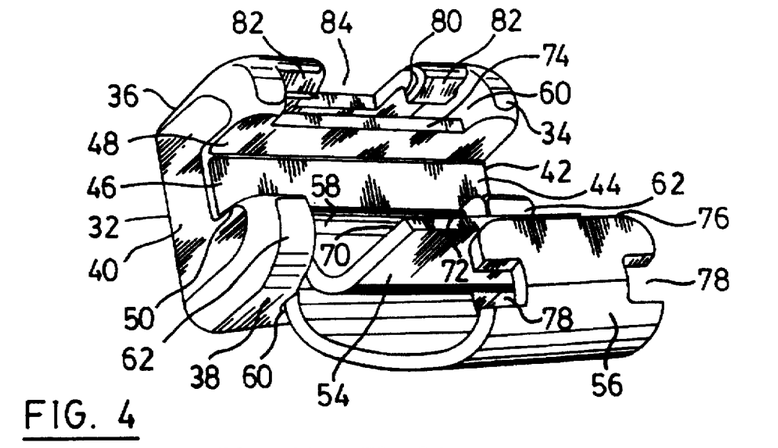
FIG. 4 is a perspective view from the lingual and occlusal of a bracket which is a first embodiment, for use with arch wires of rectangular transverse cross section, and shown with its ligating latch spring member in full slot open position.
Figure 5:
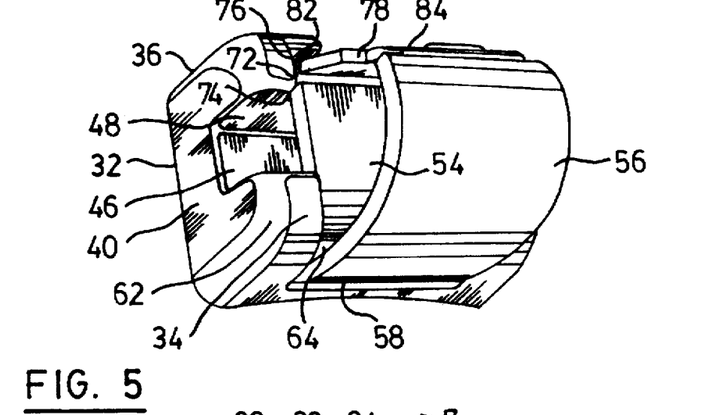
FIG. 5 is a similar view of the bracket of FIG. 4 showing the ligating inner portion of the spring member in ligating position in which it has closed the mouth of the arch wire slot, and with the latching outer portion not yet in latching engagement with the bracket body.
Figure 6:
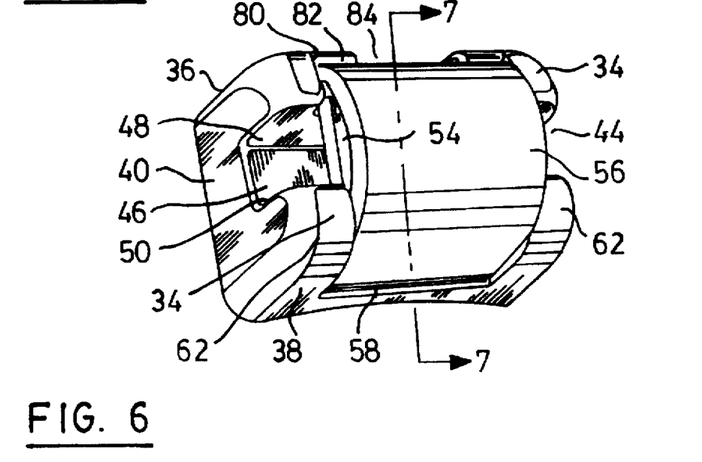
FIG. 6 is a similar view of the bracket of FIG. 5 showing the latching outer portion of the spring member now in latching engagement with the bracket body.
Figure 7:
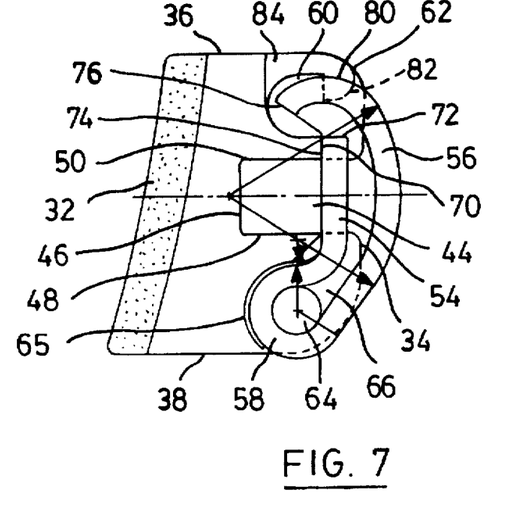
FIG. 7 is a cross section through the bracket of FIGS. 4-6, taken on the line 7—7 in FIG. 6.

FIGS. 1 through 3 each shows a respective tooth 20 having a labial surface 22 and a lingual surface 24. A bracket 26 of the invention is attached to each lingual surface, as by a suitable cement, while for comparison as to size and use a Hanson SPEED System bracket 28 is shown cemented to the labial surface of each tooth. Gum tissue surrounding the teeth has the reference 30. All of the brackets illustrated are intended for use with the so-called straight wire technique with which each bracket is attached to its respective tooth in an attitude such that, as the arch wire attempts to return to its preformed arch shape and straight as seen in a labial-lingual plane, the tooth is moved toward its desired optimized position and attitude. In order for the arch wire to be straight at the conclusion of the procedure the brackets for different teeth must accommodate for the very different inclinations of the tooth surfaces to which they are attached. There are two main methods by which this is done, either by suitable shaping of the bracket bases and of their base surfaces that contact the teeth surfaces, or by changing the inclination of the arch wire slots. FIGS. 1-3 show both methods with the first method used in the brackets of the invention and the second method used in the Hanson brackets.

Thus, in the brackets of the invention as shown herein all of the torque requirements (rotation about a mesial distal axis), angulation requirements (rotation about a labial lingual axis), and first order pre-adjustments, are obtained by suitable shaping of the bracket bases, particularly of the labial surface thereof surface that engages the tooth lingual surface, and by variation of the base thickness, so that when the teeth are in their optimum attitude and rotational position all of the lingual faces and the lingually opening slots are aligned. FIG. 1 shows the shape of the base, and the slot inclination, for a bracket intended for attachment to an upper first bicuspid, FIG. 2 shows them for a bracket for an upper first central incisor, and FIG. 3 shows them for a bracket for an upper first molar. Shapes required for the other teeth will be apparent to those skilled in the art and need not be described in further detail herein.

The second method of slot inclination can also be used in the brackets of the invention. With some brackets the inclination of the slot may be so extreme that, for example, in a bracket fixed to the lingual surface of a central incisor, it opens mainly to the occlusal and very little to the lingual; nevertheless such a bracket is within the scope of the language of the appended claims. The brackets shown in the other drawings have bodies that adapt them for attachment to a first bicuspid, this particular tooth usually having lingual and labial surfaces that diverge by only 7°–8°.

Again for convenience in description the brackets are described as having specific named surfaces but, as will be apparent, smooth exterior contours can only be achieved by avoiding sharp edge junctions, and the various surfaces therefore usually merge smoothly with one another without a definite junction between them being apparent.

Figure 13:
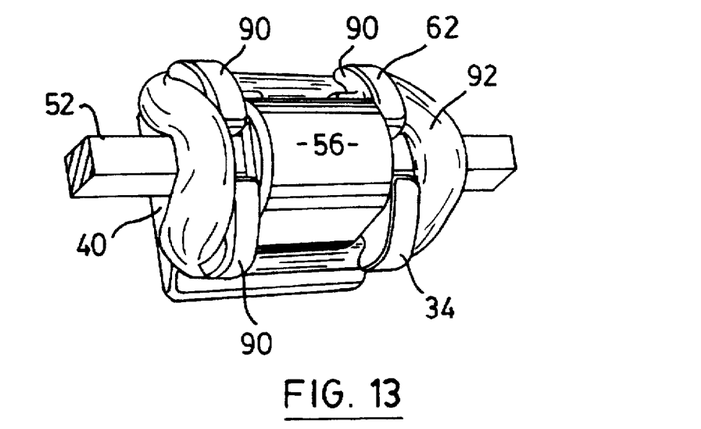
FIGS. 13 and 14 are similar perspective views corresponding to FIG. 1, illustrating the application of the self-ligating structure of the invention to the previously commonly used double tie wing bracket, and also showing the manner in which elastomeric hoop ligatures are used therewith.
Figure 14:
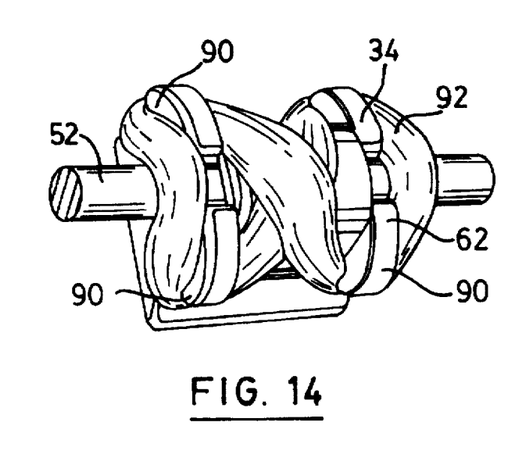
Figure 15:
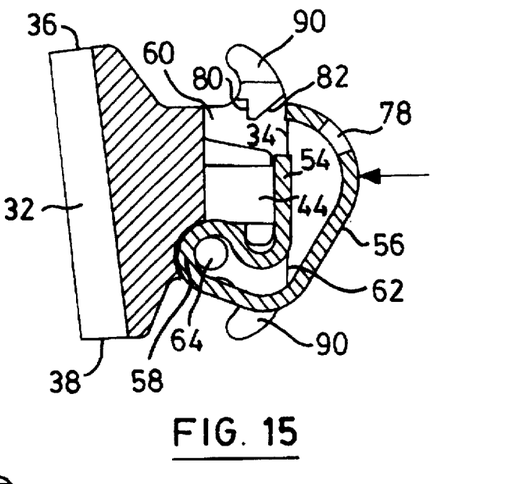
FIGS. 15 and 16 are gingival occlusal cross sections through the brackets of FIGS. 13 and 14 with the hoop ligatures removed, taken on the line 15—15 in FIG. 13.
Figure 16:
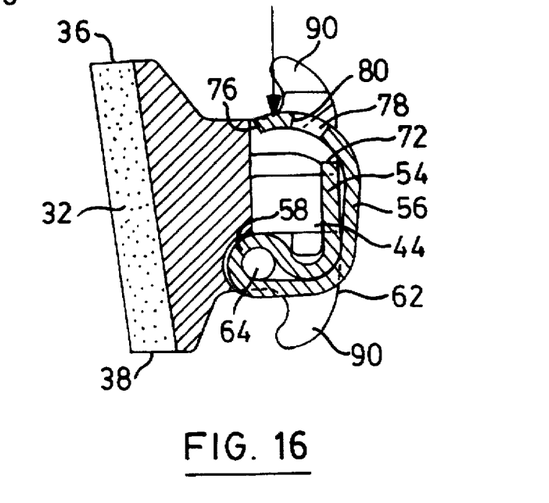

Referring now especially to FIGS. 4–7, each bracket body has labial, lingual, gingival, occlusal, mesial and distal surfaces 32, 34, 36, 38, 40 and 42 respectively. All of the brackets are shown as ready for mounting on the respective tooth 20 by cementing, as increasingly is preferred, although they could also be mounted by the older method of attaching them to respective tooth-embracing bands, which is not shown. Bands are still sometimes used in certain procedures where cementing to the teeth is not appropriate. The body is provided with a mesial-distal extending arch wire slot 44, which in this embodiment is of rectangular transverse cross section in the gingival-occlusal direction, the slot opening to the lingual surface 34 and having labial, gingival and occlusal surfaces 46, 48 and 50 respectively. The slot receives an arch wire 52 (see FIGS. 9, 10, 13 and 14), which usually in the early stages of a procedure is of circular cross section (FIG. 14), and which subsequently is replaced by one of D-shape cross section (FIGS. 9 and 10) or rectangular cross section (FIG. 13) for final control of tipping of the teeth into position. Means for retaining the arch wire in the slot, and for pressing it resiliently into engagement with the slot lingual face 46, comprise a self-ligating latching spring member of thin flat springy metal. For convenience in language the member is referred to herein as being generally U-shaped, in that it comprises two arm portions, namely an inner ligating portion 54 and an outer latching portion 56, joined by a connecting portion 58 of part circular shape, in this embodiment a little more than semi-circular shape. The two arm portions 54 and 56 are not parallel to one another but each is shaped to enable it to perform its required function, as will be described below. The spring member is accommodated in a substantial gingival occlusal extending recess 60 in the bracket body opening to the body lingual side and having two equal symmetrical spaced shoulders 62 on either side, the gingival occlusal continuity of the shoulders being interrupted by the intervention of the arch wire slot 44. In the fully slot closed and latched position shown in FIGS. 6 and 7 the ligating portion 54 is accommodated completely within the recess 60, as are the two end parts of the latching portion 56. The mesial distal width of the spring member is just slightly smaller than the corresponding width of the recess 60, while the smoothly curved central part of the latching portion 56 protrudes somewhat from the recess and presents a smoothly curved lingual face for any potential contact with the tongue and the mouth inner surfaces.

The spring member is pivotally mounted in the bracket body for movement between slot open and closed positions by two coaxial cylindrical pivot posts 64 that protrude toward one another from the facing walls of the parts of the shoulders 62 that lie between the slot and the body occlusal surface 38. The posts, a part-cylindrical recess 65 in the bracket body, and the adjacent parts of the walls cooperate to constitute a semi-cylindrical enclosure 66 of annular transverse cross section in which the part semi-circular spring member connecting portion 58 rotates. While the member is in unconstrained condition, and before it is mounted on the posts 64, the outside radius of the part circular part of the connecting portion 58 is larger than the inside radius of this enclosure. When mounted the connecting portion is therefore strained radially inward to the smaller radius of the enclosure, with the result that as it is urged radially outward by its resilience it frictionally engages the bracket body and the posts in three spaced mesially-distally extending contact areas 68 (see FIG. 9), thus providing smooth friction-damped pivoting motion of the member between these positions. This motion is without play and is with sufficient friction for the member normally to remain in a position to which it has been placed by the orthodontist until positively moved from that position. By way of example, in a particular preferred embodiment, the unmounted connecting portion of the spring member has an outside radius of 0.305 mm (0.012 in) while the enclosure inside radius is 0.275 mm–0.292 mm (0.011 in–0.0115 in).

During the early stages of a procedure it is unlikely that an arch wire inserted into the slot 44 will be fully accommodated within the slot, but instead will at least attempt to protrude out of the slot mouth and/or rotate in the slot. As the spring member is moved toward the slot closed position shown in FIG. 4 the ligating portion 54 engages the wire and presses it labially into the slot, this action continuing with rotation and bending of the adjacent portions of the wire until the spring member is in the full slot closed position with the latching portion 56 latched to the body, as will be described below. The closing movement usually thereby stresses both the arch wire and the ligating portion 54, and it is a most important advantage of self ligating brackets that the ligating member is able to contribute accurately and at all times to the restoring force urging the teeth to their final optimum positions. This is especially important in the final stages of the procedure, since it reduces the number of changes of arch wire required, enabling relatively very stiff arch wires to be used earlier in the procedure without applying excessive force to the brackets and teeth. Since this particular bracket is intended for use with arch wires of rectangular transverse cross section, the part of the inner ligating portion 54 that closes the slot opening is flat.

In the initial stages of a procedure low force undersized round cross section wires or multi-strand cables usually are used that are a loose fit in the slot, so as to avoid frictional binding which can inhibit movements involved in the "unravelling" of the crowded teeth to their desired aligned configuration. In such cases it is preferred that any action of the relatively strong ligating spring portion is at least limited, and perhaps completely prevented. To this end border part 70 of ligating portion at its free end 72 engages a mesial distal extending lingual surface 74 bordering the gingival edge of the arch wire slot to limit the movement of the ligating portion toward the labial.

As seen from the mesial or distal the latching portion 56 is convex toward the lingual and is smoothly curved from its junction with the connecting portion 58 to its free end 76 in order to provide a smooth exterior surface, this being the surface, together with the lingual surfaces of the body shoulders 62, that are most likely to be contacted by the tongue and the inner walls of the mouth. In some embodiments the part of the ligating portion bordering the free end may be flat, since in the slot closed position this part is completely within the recess 60. In this embodiment latching means for effecting the required latching engagement between the latching portion 56 and the bracket body comprise two symmetrical rectangular shaped latch notches 78 respectively in the mesial and distal edges of the latching portion adjacent to its free end, the notches cooperating with registering occlusally extending latch sears 80 on the body, the sears protruding mesially and distally from the facing walls of the body shoulders 62. The sequence of action as the latching portion is latched and unlatched will be seen by reference to FIGS. 4 through 6. As the spring member is rotated from the slot open position shown in FIG. 4 toward the latched and slot closed position shown in FIG. 6, the ligating portion engages the arch wire and thereafter the border part 70 is stopped in further movement by its engagement with the lingual surface 74; subsequently the latching portion free end 76 engages respective lingually occlusally inclined faces 82 of the latch sears, these faces constituting ramps producing occlusal movement of the free end 76 until the latch sears 80 are engaged in the latch notches 78, whereupon the free end moves gingivally under the urge of the spring member into the fully latched position.

Disengagement of the latches is produced by insertion of a suitable pointed tool (not shown) occlusally through a release opening 84 in the gingival surface 34, provided for that purpose between the two sears 80, the tool engaging the latching portion free end and pressing it occlusally against the spring urge until the latches are disengaged, whereupon the spring member can be rotated back to the slot open position.

Other latching means structures can also be used, for example that employed in the brackets shown and described in my U.S. Pat. No. 5,224,858, issued 06 Jul., 1993, the disclosure of which is incorporated herein by this reference. In these brackets the latch sears protrude mesially and distally toward each other instead of occlusally, and the end part of the latching portion 56 between the cooperating notches would in such a structure be provided with a central slot to permit the resulting end parts to move together for engagement of the latches, and to permit disengagement of the latching sears from the notches by squeezing the end parts together, using for example a small pair of pliers.

The use of a single spring element that serves both as a ligating and latching means considerably simplifies the bracket structure, while the use of an integral two armed spring member, in which one arm is employed as the ligating spring means while the other is employed as the latching spring means, permits each arm to be shaped and otherwise designed to ensure that it will perform its principal function without constraint caused by any requirement to perform multiple functions. Nevertheless, since the two portions 54 and 56 are integral and solidly connected together by the connecting portion 58, their spring actions are conjoined and reinforce one another in urging the arch wire into the slot and in holding the latches in the latched condition, so that the required spring actions extend over the full length of the member, easing the requirement for very high modulus materials in obtaining strong enough springs of such tiny dimensions.

This particular ligating latch spring member structure also provides an opportunity of adjusting the spring force for individual brackets by forming the members with different amounts of preloading before the bracket is assembled. Thus, the preload force is increased by forming the spring member with its arms increasingly widely spaced, so that they must increasingly be compressed together for the member to be moved into the fully latched condition. The amount by which an arch wire is permitted to protrude from the slot, and the corresponding amount of ligating force applied by the ligating portion 54, is also easily controlled by adjustment of the radius of curvature of the middle part of the latch portion 56, so that the distance through which the ligating portion can move before it is positively stopped by engagement with the lingual surface of the latching portion is thereby adjusted.

A continuing problem encountered with self-ligating brackets employing metal ligating springs results from the extremely small size of the brackets. Because of the requirement for high modulus metals, and the highly corrodible environment of the mouth, stainless steels have been used almost universally hitherto. Although stainless steels of the highest practical modulus are used the tiny springs are stressed very close to the elastic limit of the metal as they are moved between the slot open and closed positions, and the amount of displacement required to exceed the elastic limit is relatively small. Once that limit has been exceeded, for example by the operative carelessly moving the spring and/or attempting to force the spring to close over a stiff arch wire that protrudes too far out of the slot, then it may take such a permanent set that it can no longer function as a spring. This may require the bracket to be replaced completely, since it is not usually convenient for the orthodontist to replace the spring "in situs", especially since mounting the spring on the bracket body brings it close to the elastic limit; such replacement is of course inconvenient and unpleasant both for the patient and the orthodontist.

A new family of nickel-titanium alloys has been developed that are rapidly finding use in the fabrication of arch wires, ligating and traction springs, the most important characteristic of these alloys being their extraordinarily high elasticity with corresponding resistance to overstressing and permanent deformation, as compared to the stainless steels. Their elasticity is such that the wires and springs are not overstressed, and can regain their original shape, when subjected to strains as high as about 8%, as compared to the maximum for stainless steels of about 0.5%; for this reason they are commonly referred to as superelastic metal alloys. Another characteristic is that springs fabricated from these alloys are able to provide a relatively constant restoring force over the much wider ranges of deflection that they are able to tolerate. The atomic structure which produces this superelasticity also causes the alloys to exhibit a so-called memory phenomenon, whereby articles made of them can be bent from a desired original "memory" shape to a new quite different shape and set in that latter shape by suitable heat treatment; subsequently if heated above a transformation temperature they will return to the original memory shape. For this reason they are also commonly referred to as superelastic shape recovery metal alloys. An example of successful products made from these alloys are multi-strand cables that are increasingly being employed to form arch wires such as are described and claimed in my U.S. Pat. No. 5,344,315, issued 06 Sep., 1994, the disclosure of which is incorporated herein by this reference. An arch wire of this material can be bent sufficiently to be engaged in the slots of highly relatively displaced brackets to an extent that would be impossible with stainless steels, or if possible would cause the application of dangerously high forces to the teeth and gums.

A preferred family of superelastic shape memory alloys is nickel/titanium, usually with a nominal atomic composition of 60%:60% nickel and titanium, but with small additions of copper, iron, cobalt or chromium, the alloy being subjected to a heat treatment to develop the desired characteristic. One particularly useful alloy in this family comprises 55% nickel and 45% titanium, while another comprises equal amounts of nickel and titanium with 10 atomic % of copper. Other alloys are also known such as copper/zinc/aluminium (usually 15–25 weight % zinc, 6–9 weight % aluminium and the balance copper); copper/zinc/aluminium/manganese; copper/aluminium/nickel (usually 13–14 weight % aluminium, 3–4 weight % nickel and the balance copper); and copper/aluminium/nickel/manganese. At this time the nickel/titanium alloys are preferred in that they have the greatest ductility, more recoverable motion, excellent corrosion resistance comparable to series 300 stainless steels, stable transformation temperatures for shape recovery, high biocompatibility, and the ability to be electrically heated for shape recovery.

The benefit of the greater tolerance for displacement of both the ligating and the latching portions of the spring member provided by the use of these superelastic shape memory metal alloys are such that they are to be preferred, despite their higher cost and their lower strength modulus as compared with the suitable stainless steels, so that the spring members must usually be somewhat thicker. Nevertheless stainless steel ligating latch spring members can of course also be successfully used with these new brackets.

Figure 8:
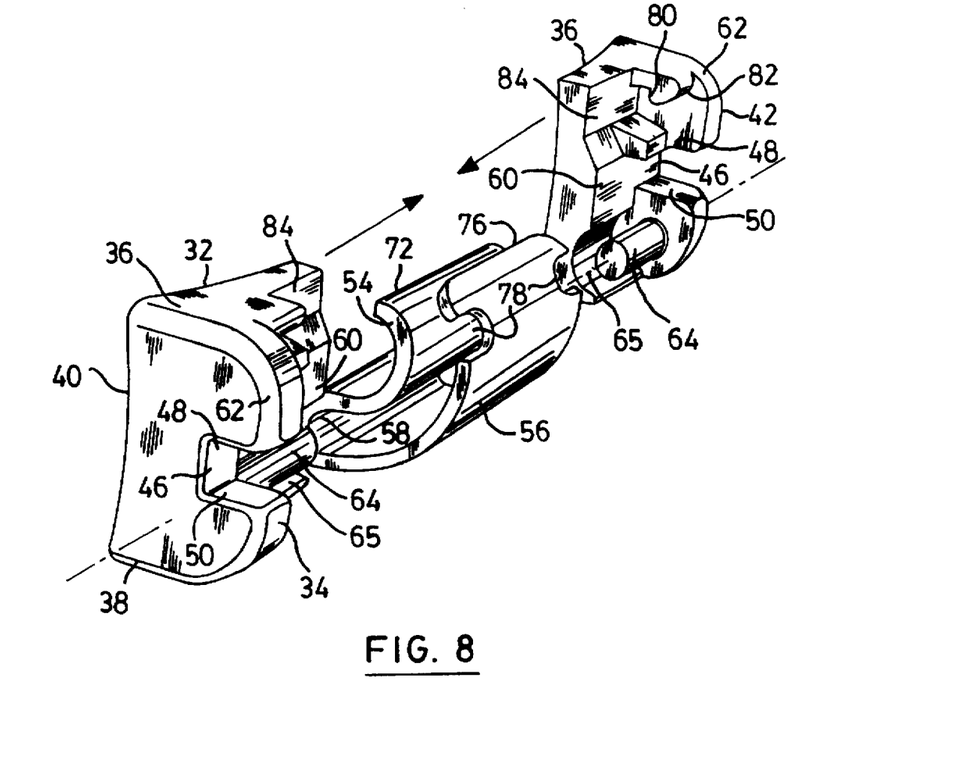
FIG. 8 is an exploded perspective view from the lingual and mesial of a bracket, showing the manner in which it is fabricated as two mirror image halves, the two halves being fastened together after mounting the spring member between them to complete the bracket.

FIG. 8 shows a simple and effective way in which the brackets of the invention can be assembled using only three parts. The bracket body is made as two mirror image parts, each having a cylindrical mesial distal extending pivot post 64 extending mesially or distally respectively therefrom. The posts are inserted into the spring member connecting portion from the sides and the two parts moved together until the two body parts can be fastened together along their butting junction, as for example by laser welding, to complete the body and at the same time to retain the spring member thereon.

Figure 9:
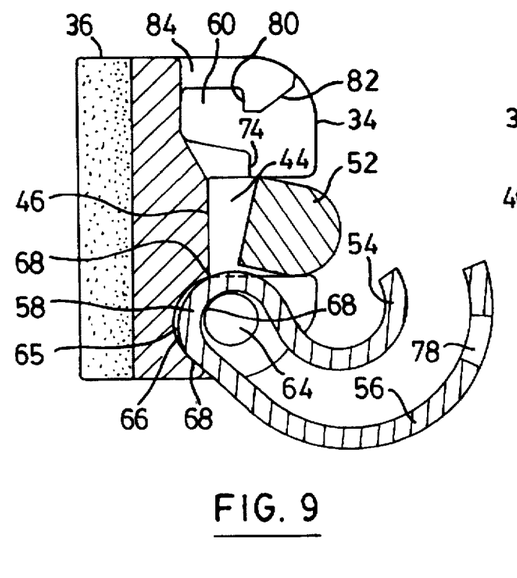
FIGS. 9 and 10 are cross sections similar to FIG. 7 through a bracket for use with arch wires of D shape transverse cross section, the Figures showing the spring member respectively in full slot open and closed positions.
Figure 10:
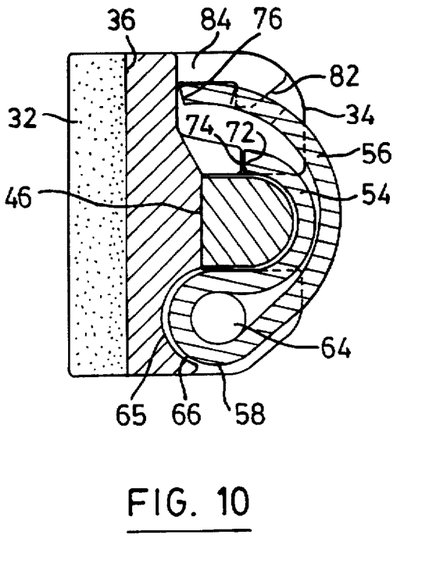

FIGS. 9 and 10 show a bracket of the invention for use with an arch wire 52 of D-shape transverse cross section, the wire being inserted in the slot with its convex face toward the lingual. In such an application the part of the inner ligating portion 54 that closes the slot opening is of convex transverse cross section toward the lingual, the shape being such that in the slot closed position, and with the tooth in the final position and orientation, as shown in FIG. 10, it embraces and conforms closely to the wire convex face. In such a bracket the free end 72 of the ligating portion butts directly against the bracket body lingual surface 74 when the tooth is in the final position and orientation.

FIGS. 9 and 10 also illustrate the excellent precise angular control achievable with brackets of the invention when used with D-shape or rectangular arch wires 52 operating in a rectangular cross section slot. In practice, for example, a standard gingival-occlusal dimension for an arch wire slot is 0.66 mm–0.0 mm and +0.013 mm (0.032 in–0.0 in and +0.0005 in), while the largest wire used has a nominal gingival-occlusal dimension of 5 0.53 mm (0.021 in), but is more usually 0.52 mm (0.0205 in); wires of smaller dimension such as 0.50 mm (0.020 in) are also commonly used. The shape control obtainable in commercial practice is much greater than the dimension control available and a wire that is rotationally displaced by even a very small angle, as shown in FIG. 9, is subjected to a restoring torque moment, producing the required rotation about a mesial distal axis, by the ligating portion 54 until, as shown in FIG. 10, the flat labial face of the wire is flat against the lingual slot surface 46, while the labial face of the ligating portion is fully engaged over its entire surface with the lingual face of the wire, whether flat or convex. A similar precise restoring effect will be produced if the protrusion of the arch wire from the slot is caused by rotational misplacement of the tooth about the gingival-occlusal axis. The brackets of the invention are also readily adaptable for use with arch wires of other transverse cross sections, such as the special cross section shown in my U.S. Pat. No. 4,492, 573, referred to above.

Figure 11:
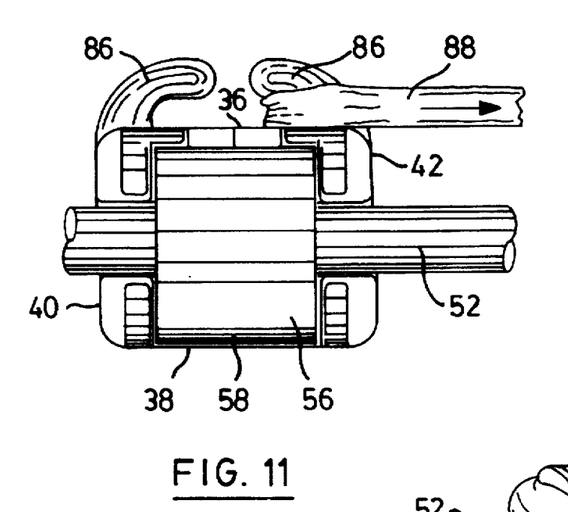
Figure 12:
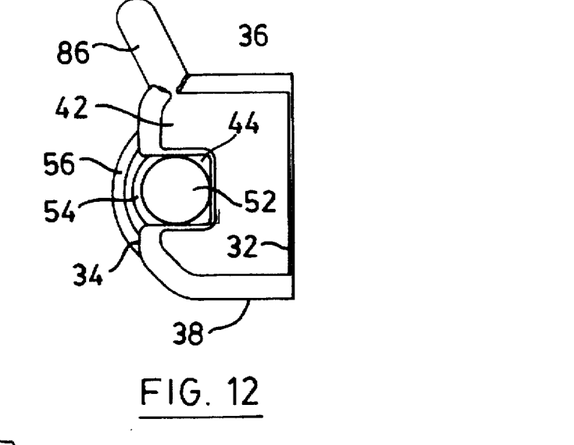

Provision must be made for the attachment to selected ones of the brackets of traction springs, elastic hoops and other devices used in orthodontic procedures, and this usually comprises hooks or headed posts that protrude from the bracket body. A preferred form of hook for the brackets of the invention is shown in FIGS. 11 and 12, the body being provided with at least one hook member 86, preferably two, protruding therefrom, both hooks extending gingivally and each extending toward one another, either mesially or distally as required. The mesial and distal surfaces of the hook members merge smoothly with the corresponding mesial and distal surfaces of the bracket body, and the hooks are smoothly curved from the gingival to the mesial and distal respectively. With the small size of the brackets they can readily be located close to the gum line, as will be seen from FIGS. 1 to 3, and it is found necessary to incline the hooks lingually inward, as shown for example in FIG. 12 at an angle of at least about 25 degrees, so as to ensure adequate room for attachment of a device thereto, such as the elastomeric traction ribbon 88 shown in FIG. 11. Such traction ribbons are described and claimed in my U.S. Pat. No. 5,184,954, issued 09 Feb. 1993, the disclosure of which is incorporated herein by this reference. An inclination of the hooks of about 25 degrees is satisfactory for brackets intended for bicuspids and molars, but those intended for incisors and canines will usually require a greater inclination of as much as 60 degrees. Brackets of the invention intended for use in a labial procedure will usually require the hooks to be inclined labially.

FIGS. 1–3 illustrate and emphasis the small size to which it is possible to make the brackets of the invention, as compared to the size of a typical adult tooth to which the bracket is attached, and as compared to a typical Hanson SPEED system bracket. Typically one of these prior art brackets currently in use has a body that measures 2.7 mm to 3.0 mm (0.108 in to 0.130 in) in gingival occlusal dimension, 2.1 mm to 2.7 mm (0.094 in to 0.1088 in) in labial lingual dimension, and 2.7 mm to 3.0 mm (0.108 in to 0.130 in) in its widest mesial distal dimension adjacent to the lingual body surface. The spring ligating member is of stainless steel of about $28-29 \times 10^6$ psi elastic modulus (which is a measure of its stiffness), and measures 0.125 mm (0.005 in) in thickness and 1.57 mm to 1.83 mm (0.062 in to 0.072 in) in the mesial distal dimension. By comparison a bracket of the invention as illustrated in the majority of the Figures measures 1.70 mm to 1.88 mm (0.067 in to 0.074 in) in gingival occlusal dimension, as low as 1.17 mm (0.046 in) in labial lingual dimension, and 2.5 mm (0.10 in) in mesial distal dimension. The spring latching member 56 is of a nickel/titanium superelastic shape memory alloy of about $10 \times 10^6$ psi elastic modulus at body temperature (38.5° C.), the alloys being somewhat temperature sensitive and, for example, the modulus of this particular alloy drops to about $7 \times 10^6$ psi at a temperature of 21.3° C.). The member measures 0.127 mm to 0.178 mm (0.005 in to 0.007 in) in thickness and 1.52 mm (0.060 in) in the mesial distal dimension.

Situations may arise in an orthodontic procedure that the use of an external ligature additional to, or even replacing, the ligation available from the bracket ligating spring, for example where initially a tooth is grossly displaced. Another factor to be considered is that orthodontists who have been using external ligatures in their procedures may be somewhat reluctant initially to adopt a completely new procedure which does not permit them at least the opportunity of using their established skills in this regard, and would therefore be reassured if provided with a self ligating bracket that at the same time did have some provision for the use of an external ligature whenever the orthodontist felt it appropriate to do so. One form of bracket providing such a facility is shown in FIGS. 13–16, in which the ligating latch spring member of the invention has been combined with a bracket body of the well known double tie wing construction extensively used hitherto with external wire tie wires and elastomeric hoop ligatures. The body has two pairs of tie wings 90 for the reception and retention of an external ligature, such as the elastomeric loop ligatures 92 shown in FIGS. 13 and 14, the two figures showing two different ways of using such ligatures. The tie wing pairs may be regarded essentially as gingival and occlusal extensions of the body shoulders 62 of the previously described brackets, being spaced mesially distally from one another, with the two wings of each pair extending gingivally and occlusally away from one another. The ligating latch spring member is disposed on the body in recess 60 between the two pairs of tie wings.

I claim:

1. An orthodontic bracket comprising:

a bracket body having labial, lingual, gingival, occlusal, mesial and distal surface portions, the body having at least one mesial distal extending pivot post and having a mesial distal extending arch wire slot having a slot opening that opens to the lingual surface portion; and a ligating latch spring member comprising a ligating portion and a latching portion joined at adjacent ends by a connecting portion;

the spring member connecting portion being wrapped around the pivot post whereby the spring member is mounted on the body for pivoting movement between an unlatched slot open position in which the slot labial opening is open for insertion of an arch wire into the slot, and a latched slot closed position in which the ligating portion extends across the slot labial opening to thereby close the slot opening for retention of an arch wire in the slot by the ligating portion and in which the spring member is latched in the slot closed position by latching engagement between the latching portion and the bracket body;

wherein the ligating portion of the ligating latch spring member has a free edge border portion further from its junction with the connecting portion, and wherein in the slot closed position the free edge border portion of the ligating portion engages a surface bordering the arch wire slot to limit the movement of the ligating portion toward the slot.

2. A bracket as claimed in claim 1, wherein the ligating portion of the ligating latch spring member has a free edge further from its junction with the connecting portion, and wherein in the slot closed position of the ligating portion the free edge engages a surface bordering the arch wire slot to limit the movement of the ligating portion toward the slot.

3. A bracket as claimed in claim 1, and for use with arch wires of rectangular transverse cross section having flat labial and lingual surfaces, wherein a part of the ligating portion that closes the slot labial opening is flat for engagement with the flat lingual surface of the arch wire.

4. A bracket as claimed in claim 1, and for use with arch wires that are of D-shape transverse cross section having flat labial surfaces and convex lingual surfaces, such wires being inserted in the arch wire slot with the convex face of the wire toward the lingual, wherein a part of the ligating portion that closes the slot opening is of convex transverse cross section such that in the slot closed position it embraces and conforms closely to the arch wire convex lingual surface.

5. A bracket as claimed in claim 1, wherein the bracket body has therein a part cylindrical recess having an inner wall;

wherein the pivot post is cylindrical and is coaxial with the part cylindrical recess to form a chamber of annular transverse cross section between them;

wherein the spring member connecting portion is part circular in transverse cross section and is movable within the part cylindrical recess;

and wherein the external radius of the part circular spring member connecting portion is larger than the internal radius of the part cylindrical recess, so that when mounted the connecting portion is strained radially by its resilience to frictionally engage with the inner wall of the part cylindrical recess and with the pivot post for frictional damping of the pivoting movement of the spring member on the pivot post.

6. A bracket as claimed in claim 1, wherein the bracket body is made as two mirror image parts which butt one another at a junction, and between which the ligating latch spring member is mounted, the two body parts being fastened together at their junction to retain the member thereon.

7. A bracket as claimed in claim 6, wherein each body part has a cylindrical mesial distal extending pivot post extending mesially or distally therefrom, and the ligating latch spring member is mounted on the posts for pivoting movement relative to the bracket body.

8. A bracket as claimed in claim 1, wherein the latching portion of the ligating latch spring member has mesial and distal edges and a free end further from its junction with the connecting portion; and wherein means for effecting latching engagement between the spring member latching portion and the bracket body comprise notches in the mesial and distal edges of the latching portion adjacent to its free end, and cooperating occlusally extending latch sears on the bracket body which engage in the respective notch to effect the latching, the spring member latching portion free end moving in gingival occlusal direction to engage and disengage the latches.

9. A bracket as claimed in claim 8, wherein the latch sears have respective lingual occlusal inclined cam faces that are engaged by the free end of the latching portion in its movement toward the latched position, each cam face constituting a ramp producing occlusal movement of the free end until the latch sears are engaged in the latch notches.

10. A bracket as claimed in claim 1, wherein the ligating latch spring member is made of a shape memory metal.

11. A bracket as claimed in claim 10, wherein the ligating latch spring member is made of a nickel titanium shape memory alloy.

12. A bracket as claimed in claim 1, wherein the bracket body has protruding therefrom a hook member that extends gingivally and either mesially or distally for attachment of a traction spring member and the like to the bracket body.

13. A bracket as claimed in claim 12, wherein the bracket body has protruding therefrom two hook members that extend gingivally and respectively mesially and distally toward one another for attachment of a traction spring member and the like to the bracket body.

14. A bracket as claimed in claim 1, wherein the bracket body has two pairs of tie wings for the reception and retention of an external ligature;

wherein the pairs of tie wings are spaced mesially distally from one another, and the two wings of each pair extend gingivally and occlusally away from one another; and wherein the ligating latch spring member is disposed on the body between the two pairs of tie wings.

15. An orthodontic bracket comprising:

a bracket body having labial, lingual, gingival, occlusal, mesial and distal surface portions, the body having a mesial distal extending arch wire slot having a slot opening that opens to the lingual surface portion; and a ligating latch spring member comprising a ligating portion and a latching portion joined at adjacent ends by a connecting portion;

the spring member being mounted on the body for movement between an unlatched slot open position in which the slot labial opening is open for insertion of an arch wire into the slot, and a latched slot closed position in which the slot labial opening is closed for retention of an arch wire in the slot by the ligating portion and the spring member is latched in the slot closed position by latching engagement between the latching portion and the bracket body;

wherein the ligating latch spring member is mounted on the body for pivoting movement thereon on at least one mesial distal extending pivot post about which the spring member connecting portion is wrapped;

wherein the bracket body has therein a part cylindrical recess having an inner wall;

wherein the pivot post is cylindrical and is coaxial with the part cylindrical recess to form a chamber of annular transverse cross section between them;

wherein the spring member connecting portion is part circular in transverse cross section and is movable within the part cylindrical recess;

and wherein the external radius of the part circular spring member connecting portion is larger than the internal radius of the part cylindrical recess, so that when mounted the connecting portion is strained radially by its resilience to frictionally engage with the inner wall of the part cylindrical recess and with the pivot post for frictional damping of the pivoting movement of the spring member on the pivot post.

16. A bracket as claimed in claim 15, wherein the bracket body is made as two mirror image parts which butt one another at a junction, and between which the ligating latch spring member is mounted, the two body parts being fastened together at their junction to retain the member thereon.

17. An orthodontic bracket comprising:

a bracket body having labial, lingual, gingival, occlusal, mesial and distal surface portions, the body having a mesial distal extending arch wire slot having a slot opening that opens to the lingual surface portion; and a ligating latch spring member comprising a ligating portion and a latching portion joined at adjacent ends by a connecting portion;

the spring member being mounted on the body for movement between an unlatched slot open position in which the slot labial opening is open for insertion of an arch wire into the slot, and a latched slot closed position in which the slot labial opening is closed for retention of an arch wire in the slot by the ligating portion and the spring member is latched in the slot closed position by latching engagement between the latching portion and the bracket body;

wherein the ligating latch spring member is mounted on the body for pivoting movement thereon on at least one mesial distal extending pivot post about which the spring member connecting portion is wrapped;

wherein the latching portion of the ligating latch spring member has mesial and distal edges and a free end further from its junction with the connecting portion; and wherein means for effecting latching engagement between the spring member latching portion and the bracket body comprise notches in the mesial and distal edges of the latching portion adjacent to its free end, and cooperating occlusally extending latch sears on the bracket body which engage in the respective notch to effect the latching, the spring member latching portion free end moving in gingival occlusal direction to engage and disengage the latches.

18. A bracket as claimed in claim 17, wherein the bracket body is made as two mirror image parts which butt one another at a junction, and between which the ligating latch spring member is mounted, the two body parts being fastened together at their junction to retain the member thereon.

19. An orthodontic bracket comprising:

a bracket body having labial, lingual, gingival, occlusal, mesial and distal surface portions, the body having a mesial distal extending arch wire slot having a slot opening that opens to the lingual surface portion; and a ligating latch spring member comprising a ligating portion and a latching portion;

the spring member being mounted on the body for movement between an unlatched slot open position in which the slot labial opening is open for insertion of an arch wire into the slot, and a latched slot closed position in which the slot labial opening is closed for retention of an arch wire in the slot by the ligating portion and the spring member is latched in the slot closed position by latching engagement between the latching portion and the bracket body;

wherein the bracket body is made as two mirror image parts which butt one another at a junction, and between which the spring member is mounted, the two body parts being fastened together at their junction to retain the spring member thereon.

20. A bracket as claimed in claim 19, wherein each body part has a cylindrical mesial distal extending pivot post extending mesially or distally therefrom, and the ligating latch spring member is mounted on the posts for pivoting movement relative to the bracket body.

* * * * *